United States Patent
Lo et al.

[11] Patent Number: 5,516,530
[45] Date of Patent: May 14, 1996

[54] POROUS SHAPED DELIVERY DEVICES AND METHOD OF PRODUCING THEREOF

[75] Inventors: Julian B. Lo, Old Lyme; Gary G. Mackay, Ledyard; Michael J. Puz, Pawcatuck, all of Conn.

[73] Assignee: Pfizer Inc., New York, N.Y.

[21] Appl. No.: 244,700

[22] PCT Filed: Nov. 4, 1992

[86] PCT No.: PCT/US92/09273

§ 371 Date: Jun. 1, 1994

§ 102(e) Date: Jun. 1, 1994

[87] PCT Pub. No.: WO93/12770

PCT Pub. Date: Jul. 8, 1993

Related U.S. Application Data

[63] Continuation-in-part of Ser. No. 811,411, Dec. 20, 1991, abandoned.

[51] Int. Cl.⁶ ........................... A61K 9/44
[52] U.S. Cl. .................. 424/473; 424/487
[58] Field of Search ............... 424/78.08, 487, 424/473

[56] References Cited

U.S. PATENT DOCUMENTS

| | | | |
|---|---|---|---|
| 3,885,026 | 5/1975 | Heinemann et al. | 424/14 |
| 4,134,943 | 1/1979 | Kaitsch et al. | 264/28 |
| 4,217,898 | 8/1980 | Theeuwes | 424/473 |
| 4,305,502 | 12/1981 | Gregory et al. | 206/532 |

FOREIGN PATENT DOCUMENTS

| | | |
|---|---|---|
| 0084705 | 11/1982 | European Pat. Off. |
| 0081912 | 11/1982 | European Pat. Off. |
| 9109591 | 7/1991 | WIPO |

*Primary Examiner*—Edward J. Webman
*Attorney, Agent, or Firm*—Peter C. Richardson; Gregg C. Benson; A. Dean Olson

[57] ABSTRACT

High strength, high porosity delivery devices have a shaped surface and disintegrate quickly in an aqueous medium. The devices can be prepared by disposing a formulation in a die to form a frozen predevice. A second die is contacted with the frozen formulation surface at a pressure and temperature for a time sufficient to locally momentarily liquify and shape the device surface. The shaping is followed by lyophilization.

15 Claims, 2 Drawing Sheets

POROUS SHAPED DELIVERY DEVICES AND METHOD OF PRODUCING THEREOF

This application was filed under 35 U.S.C. §371 based on PCT/US92/09273, which was filed on Nov. 4, 1992, which was a continuation-in-part of U.S. application Ser. No. 07/811,411 which was filed on Dec. 20, 1991 and is now abandoned.

BACKGROUND OF THE INVENTION

This invention relates to delivery devices, particularly pharmaceutical tablets, and methods for making thereof.

Pharmaceutical tablets are often administered orally. A rapid disintegration of the tablet in the mouth without mastication or water facilitates administration to patients in general, and to the very young, the elderly, and to non-human animals, in particular.

One type of oral dosage form which is designed to address the problem of swallowing is known as "chewable tablets". These tablets, however, are not fully satisfactory because they require mastication.

Another type of oral dosage form known as the "effervescent tablet" comprises solid adjuvants of an acid and a base. The reaction between the acid and the base in the presence of water gives off carbon dioxide which "blows apart" the tablet to facilitate its dissolution. One type of effervescent tablet that must dissolve in a glass of water for administration requires that the patient drink the water. Aside from the problem of leaving a small amount of residual active agent in the glass, this dosing method is impractical for very young patients. Another type of effervescent tablet that "bubbles" and then dissolves in the mouth is also objectionable to some patient populations, especially the very young. Both types of effervescent tablets are thus not fully satisfactory.

Yet another type of oral dosage form known as the "enteric tablet" is designed to release the pharmaceutical agent in the upper small intestine. A limitation of enteric tablets is that those that fail to disintegrate rapidly in the intestine could pass the "window of absorption" and result in poor bioavailability.

One type of non-oral dosage form known as the birth control pessaries often takes as long as ten minutes to release the foaming agent. For obvious reasons, it is desirable for this type of dosage form to disintegrate rapidly.

Tablets that disintegrate rapidly in an aqueous environment are often formulated with disintegration agents, such as starch, microcrystalline cellulose, carboxymethylcellulose sodium, and sodium starch glycolate, etc. These tablets disintegrate at an unsatisfactory rate for some applications described above.

An increased disintegration rate can be obtained by increasing the porosity (void spaces) of the tablet. Void spaces in the tablet matrix facilitate the permeation of water to rapidly erode the entire tablet. It is easily understood that a higher porosity of the tablet implies a faster disintegration in an aqueous environment. It is therefore desirable to obtain tablets of the highest porosity technically achievable.

U.S. Pat. No. 3,885,026 discloses a process for the production of porous tablets. In this process, a solid volatilizable adjuvant is incorporated in the tablet formulation. The tablet is formed by compression, and the volatilizable adjuvant is removed by sublimation or thermal decomposition. Exemplary volatilizable adjuvant include urethane, urea, ammonium bicarbonate, hexamethylenetetramine, benzoic acid, phthalic anhydride, naphthalene and camphor. The maximum porosity obtained according to this patent is 50% and preferably 10 to 30%. Strong tablets of a porosity higher than 50% are difficult to produce by this method.

U.S. Pat. No. 4,134,943 discloses the production of porous tablets by mixing the tablet components with a liquid solvent which is inert towards the tablet components. Suitable solvents include water, cyclohexane, benzene, etc., which freeze at a temperature from about $-30°$ to $+25°$ C. The solvent constitutes about 5 to 80% by weight of the total mixture. The mixture is divided or sprayed into small particles or droplets which are subsequently frozen into solid flowable granules. These granules are pressed into tablets at a temperature below the freezing point of the solvent, and then the solvent is sublimed from the tablets. The porosity of the resultant tablets corresponds to the amount of solvent that is removed from the tablet. The maximum porosity of the tablets produced by this method is 80%. The method of production in this patent is relatively complex since it involves the preparation of frozen granules.

Finally, U.S. Pat. Nos. 4,305,502 and 4,371,516 disclose the production of shaped articles by freezing, in a mold, a water-based pharmaceutical composition, and subliming the water from the frozen composition to form porous articles. These processes do not include compression of the articles and therefore lack the ability to produce a specifically desired shape of the article on the side of the mold that is open. Because the articles produced by this process have weak, easily broken meniscuses, U.S. Pat. No. 4,305,502 reduces the amount of handling of the articles by forming them in situ in the depressions of a filmic packaging substrate. The method in both patents allows only one side of the article to be imprinted. It is therefore difficult to include both the company logo and the drug identification on one dose unit as usually desired.

Although there are a variety of methods for making porous tablets, these methods do not adequately address all the problems. For example, processes are complex, tablets lack sufficient porosity, tablets are not shaped, tablets are weak and fragile. Accordingly, there is a continual search in this art for highly porous, strong, shaped tablets.

SUMMARY OF THE INVENTION

This invention is directed to high strength, high porosity delivery devices that have a molded shape over substantially their entire surface area and disintegrate rapidly in an aqueous medium. The tablets comprise about 5% to about 95% water soluble polymer and an active agent.

Another aspect of this invention is directed to a simple method of making strong, highly porous, shaped delivery devices. The method comprises disposing a formulation in a first die and freezing the formulation to form a frozen predevice. A second die is contacted with the frozen predevice surface at a pressure and temperature for a time sufficient to locally liquify, shape, and refreeze the predevice surface. The shaped frozen predevice is lyophilized to form the highly porous device. Preferably, the formulation includes at least one water soluble polymer and at least one beneficial agent.

This invention makes a significant advance in the field of delivery devices by providing high strength, highly porous devices that have a molded shape over their entire surface area and disintegrate rapidly in an aqueous medium. This invention also provides a simple efficient method for the production of such devices.

DETAILED DESCRIPTION OF THE INVENTION

Figure 1:
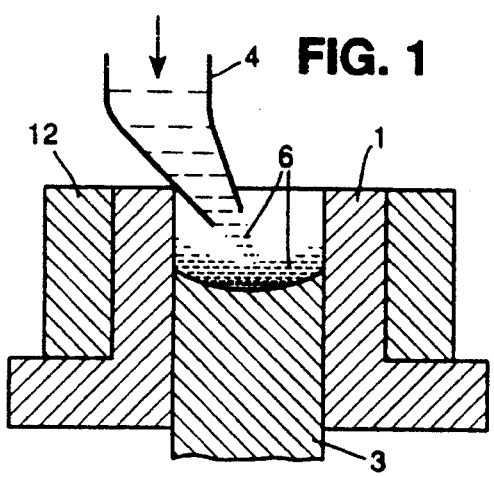
FIG. 1 is a schematic (in cross-section) illustrating the filling of a die with the liquid formulation.

Any water soluble polymer may be employed as the strengthening substance in the devices of this invention. Water soluble polymer is also meant to include lightly cross-linked fine particle polymers, for example, carbomer which is an acrylic acid polymer cross-linked with a polyalkenyl polyether. Preferably, the water soluble polymer is a film-forming polymer. By "film-forming polymers" is meant, as described in "The Theory and Practice of Industrial Pharmacy" by Lachman, Ueberman and Kanig (1970), polymers which are sufficiently soluble in the solvent and are capable of producing a strong continuous film. These water soluble polymers act as a binder to provide sufficient adhesion to enable the device to maintain its structural shape, Preferably, the water soluble polymer is gum arabic, agar, alginic acid, carbomer, carboxymethylcellulose calcium, carboxymethylcellulose sodium, carrageenan, chitosan, dextrin, gelatin, guar gum, hyaluronic acid, hydroxyethyl cellulose, hydroxypropyl cellulose, hydroxypropyl methylcellulose, methyl-cellulose, pectin, poloxamer, polyethylene glycol, polyacrylamide, polyvinyl alcohol, poly(N-vinylpyrrolidone), propylene glycol alginate, sodium alginate, tragacanth or xanthum gum. It is especially preferred that gelatin, pectin, hydroxypropyl cellulose, poly(N-vinylpyrrolidone) or carbomer be used.

Generally, the water soluble polymer comprises about 1% to about 10% of the predevice formulation composition. These quantities provide the finished device with sufficient strength and a satisfactory dissolution rate. It is preferred that about 2% to about 4% of the predevice formulation be water soluble polymer, and especially preferred that about 2% to about 3% of the prodevice formulation be water soluble polymer. These above percentages correspond to about 5% to about 95% (preferably about 5% to about 30%) of the weight of the actual device (i.e. after lyophilization).

The devices of this invention comprise, in addition to the water soluble polymer, one or more beneficial agents. The term "beneficial agents" as used in this specification and the accompanying claims includes, by way of example and not of limitation, any physiologically or pharmacologically active substance that produces a localized or systemic effect in animals. The term "animals" is meant to include mammals including human beings as well as other animals. The physiologically or pharmacologically active substance of this invention need not be soluble in water.

Examples of active substances employed in the devices of this invention include, without limitation, inorganic and organic compounds, such as drugs that act on the peripheral nerves, adrenergic receptors, cholinergic receptors, nervous system, skeletal muscles, cardia-vascular smooth muscles, blood circulatory system, synaptic sites, neuroeffector junctional sites, endocrine and hormone systems, immunological system, reproductive system, autacoid systems, alimentary and excretory systems, and inhibitors of autacolds and histamine systems. Drugs that can be delivered for acting on these systems include antidepressants, hypnotic, sedatives, psychic energizers, tranquilizers, anticonvulsants, muscle relaxants, antisecretories, anti-parkinson agents, analgesics, anti-inflammatory agents, local anesthetics, muscle contractants, antibiotics, antimicrobials, anthelmintics, anti-malarials, hormonal agents, contraceptives, histamines, antihistamines, adrenergic agents, diuretics, antiscabietics, antipediculars, anti-parasitics, anti-neoplastic agents, hypoglycemics, electrolytes, vitamins, diagnostic agents and cardiovascular drugs. Especially preferred pharmaceutical agents include ascorbic acid, acetamino-phen, acetylsalicylic acid, diphenhydramine, doxylamine succinate, meclizine, pseudoephedrine HCl, azithromycin, erythromycin, sultamicillin tosylate, amoxicillin trihydrate, sulbactam sodium, nifedipine, doxazosin mesylate, amlodipine besylate, glipizide, perbuterol HCl, fluconazole, piroxicam, toniclap, sertraline HCl, cetirizine and denofioxacin. Preferably, the formulation includes a unit dose of the beneficial agents. The amount of the beneficial agent employed is based on the clinically established efficacious dose, which ranges from about 0.01 mg to about 1000 mg. The weight ratio of said active ingredient to the carrier is in the range of 1:1 to 1:2500.

Also included in such beneficial agents are prodrugs of the abovedescribed drugs. Such drugs or prodrugs can be in a variety of forms such as the pharmaceutically acceptable salts thereof, and they need not be water soluble. It is within the scope of this invention that the devices can contain more than one beneficial agent.

The beneficial agents of this invention also include substances for which it is desirable and/or advantageous to control delivery into an environment of use. Examples of such agents, include, but are not limited to, fertilizers, algicide, reaction catalysts, enzymes, and food or drink additives.

In addition to the above described components, other common pharmaceutical excipient may be used. These excipients are generally known in the art, for example, as described in Remington's Pharmaceutical Sciences, 18th Edition (1990), particularly pages 1633 to 1638, and in the Handbook of Pharmaceutical Excipient by the American Pharmaceutical Association. Exemplary excipients include flavoring agents such as natural and artificial orange flavor, grape flavor, artificial banana flavor, strawberry flavor, cherry flavor, peppermint, fruit punch flavor and bubble gum flavor, sweetening agents such as sucrose, aspartame, and alitame, coloring agents such as FD&C red #3 and #40, FD&C yellow #5 and #6, and FD&C blue #2, lubricating agents such as magnesium stearate, sodium lauryl sulfate, talc, pelyethyleneglycols, stearic acid, hydrogenated vegetable oils, corn starch, sodium benzoate and sodium acetate, disintegrants such as corn starch, complex silicates, sodium carboxymethyl starch, microcrystalline cellulose, sodium alginate, alginic acid, cross-linked polyvinylpyrrolidone and carboxymethylcellulose sodium, diluents such as lactose, sucrose, dextrose, mannitol, xylitol, sorbitol, sodium chloride, and dibasic calcium phosphate, suspending agents such as acacia, bentonire, calcium stearate, carhomer, gelatin, guar gum, hydroxypropyl cellulose, methyl cellulose, polyvinyl alcohol, povidone, sodium alginate, tragacanth and xanthan gum, emulsifying agents such sodium lauryl sulfate, polyoxyethylene sorbitan monooleate, sorbitan monolaurate, poloxamers, lecithin, acacia, emulsifying wax, and polyethylene stearate. As is clear from the above, the same excipient may be used for different purposes within the same devices of this invention. For example, mannitol and xylitol can be used as both the diluents and the strengthening substances in the device.

The remainder of the formulation is water. The amount of water is selected to achieve the desired porosity subsequent to lyophilization.

The porous devices of this invention have sufficient porosity to provide the devices with the desired strength and dissolution rate. Preferably, the porosity is from about 85% to about 98%. The term "porosity" of a tablet as used herein refers to the void spaces created by the removal of water from the tablet by lyophilization. Since the dimensions of the lyophilized tablet are unchanged, "porosity" can be expressed either as the percentage of void spaces by volume in the lyophilized tablet, or as the percentage of water by weight in the tablet formulation prior to lyophilization. Preferably, the porosity is about 90% to about 95%. The devices have an open matrix network. This structure is expressed as a network of water-soluble carrier material having interstices dispersed throughout. The open matrix network of the carrier material is of generally low density. For example the density may be within the range of 10 to 400 mg/cm$^3$, preferably 30 to 150 mg/cm$^3$, more preferably 60 to 150 mg/cm$^3$. The density of the shaped device may be affected by the amount of pharmaceutical substance, or other chemical, or any other ingredients incorporated into the device, and may be outside the abovementioned limits for the density of the matrix network. The open matrix network, which is similar in structure to a solid foam, enables a liquid to enter the product through the interstices and permeate through the interior. Permeation by aqueous media exposes the carrier material of both the interior and exterior of the device to the action of the aqueous media resulting in rapid disintegration of the matrix network. The open matrix structure is of a porous and capillary nature which enhances disintegration of the product as compared with ordinary solid shaped pharmaceutical dosage forms, such as tablets, pills, capsules, suppositories and pessaries. Rapid disintegration results in rapid release of any pharmaceutical substance or other chemical carried by the matrix.

The porous tablets have high strength (i.e., low friability) as a result of their laminate structure. By "laminate structure" is meant that thin walls of the water soluble polymer are compacted. Between the walls are the open spaces where the water was prior to lyophilization. This laminate structure strengthens the tablet, and the open spaces (expressed as capillaries) greatly facilitate the permeation of water and the dissolution of the device.

In addition, the devices are shaped (i.e., have a predetermined molded shape) over substantially their entire surface area. By "shaped" is meant that the surface has a form that would not naturally occur through the mere action of gravity or surface tension (such as a meniscus). This molded shape may take any form, such as concave round, dual-radius, octagon, oval, or saddle, optionally with bevelled edges or shaped patterns, and preferably includes molded symbols on the surface. The symbols may include logos, brand names, drug identification, doses, etc. Advantageously, these symbols may be present on more than one "side" of the device since the devices are molded over substantially all their surface area.

The devices of this invention may be made by any process that results in the tablets having the desired combination of strength, porosity, disintegration rate and shape.

In the method of producing the shaped devices of this invention, any substantially water-soluble solid can be employed as the "strengthening substance" (i.e., the carrier) in the device. Exemplary water-soluble solids, in addition to the above polymers include, but are not limited to, vitamins such as ascorbic acid; amino acids such as glycine, arginine and phenylalanine; monosaccharides such as glucose and fructose; disaccharides such as realrose and lactose; polyhydroxy alcohols such as mannitol and xylitol, carboxylic acids such as phenylacetic acid, L-glutamic acid, adipic acid, L-tartaric acid, citric acid and succinic acid; derivatives of carboxylic acids such as urea (an amide); salts of carboxylic acids such as tartrazine (FD&C yellow #5) and sodium citrate; amines such as glutamine; alcohols such as cinnamyl alcohol; and inorganic salts such as potassium chloride, sodium chloride and monosodium glutamate.

Generally, the devices of this invention are made by freezing the desired formulation in a die and contacting another die with the exposed device surface at a pressure and temperature for a time sufficient to locally liquify, and shape the surface and then immediately re-freeze the shaped surface in situ.

The frozen device is then lyophilized. By "locally liquify" is meant sufficient portions of the formulation remain solid so that there is substantially no formulation leakage from the die. Preferably, the ingredients are combined to form a slurry, solution, or suspension using standard formulation techniques, and the resulting formulation is disposed in a die having the desired shape. The dies used in this process may advantageously have particular insignias in order to impart a logo, brand name, dose, drug identification, etc., to the finished devices. The formulation is then exposed to an environment sufficient to lower the temperature of the formulation below its particular eutectic point. Typically, for the formulations described herein, the temperature is below about 0° C. Preferably the temperature is below about −30° C.

Once frozen, a second shaped die is disposed in contact with as much of the remaining surface (i.e., the exposed surface) as is desired. Typically, substantially all of the exposed surface is formed by locally liquifying, shaping, and re-freezing the surface. The phenomenon of liquefying under pressure is due to an unusual behavior of water; i.e., the melting point of ice is decreased by increasing pressure. The localized liquification differentiates this process from processes where shaping is performed by a compression of granulated substances; upon compression of granulated substances, particles are fractured and forced close to one another and bonded by ionic or van der Weals interaction. Generally, in the present invention, the die is contacted with the exposed predevice surface at a pressure of about 0.5 kg/cm$^2$ to 9,000 kg/cm$^2$ at a temperature of from about 200° C. to about −78° C. over a period of about 1 second to about 1 minute. Preferably, the die contacts the exposed device surface at a pressure of about 450 kg/cm$^2$ to about 2500 kg/cm$^2$ and at a temperature of about −30° C. to about 60° C. for about 1 second to about 10 seconds. Clearly, there is a time-temperature-pressure dependency, and those skilled in the art can readily select the appropriate combination to achieve the desired effect (i.e., production of the devices described herein). Preferably, a mold release system is employed. This system may comprise a die formed of a conventional release type material such as polytetrafluoroethylene or anodized aluminum, or the die may be coated with conventional release films such as ethanol, calcium stearate, magnesium stearate, silicone grease or polytetrafluoroethylene.

Once molded, the frozen device is typically released from the mold and lyophilized (freeze dried)(although it need not be released for lyophilization to occur) so that the solvent (i.e., water) sublimes, resulting in the porous device described herein. The lyophilization may be performed by subjecting the molded device to reduced pressure and, if desired, to controlled application of heat to aid the sublimation. The pressure can be below about 4 mm Hg and is preferably below 0.3 mm Hg, for example 0.1 to 0.2 min. The temperature may be about −40° C. to about 20° C.

Figure 2:
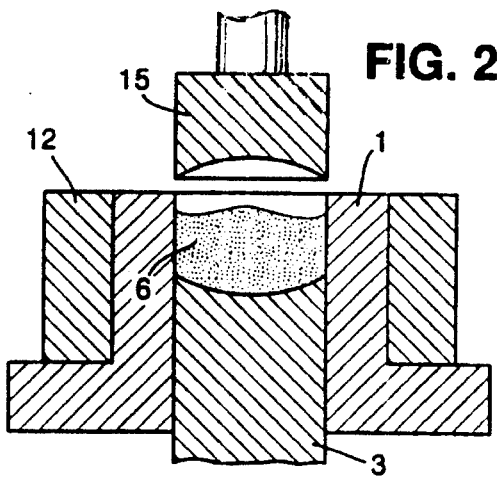
FIG. 2 is a schematic (in cross-section) illustrating the formulation-filled die being frozen.
Figure 3:
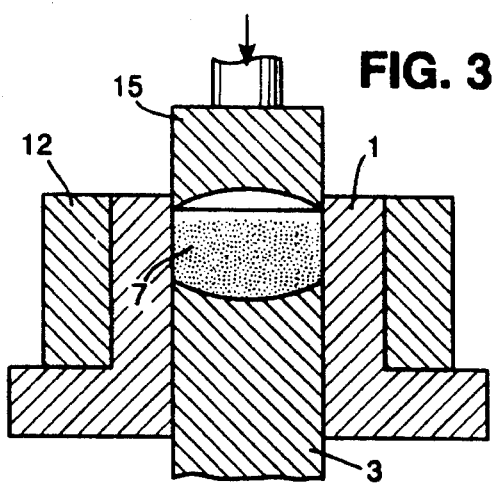
FIG. 3 is a schematic (in cross-section) illustrating contact of the top punch with the die and frozen formulation meniscus.
Figure 4:
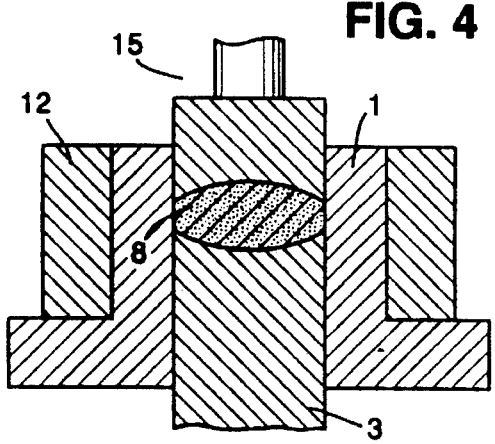
FIG. 4 is a schematic (in cross-section) illustrating the shaping of the frozen formulation by the top punch.
Figure 5:
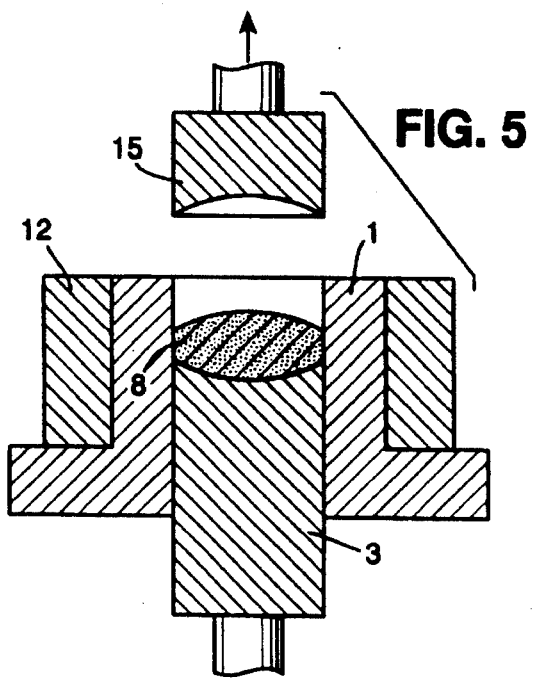
FIG. 5 is a schematic (in cross-section) illustrating the release of the top punch from the die.
Figure 6:
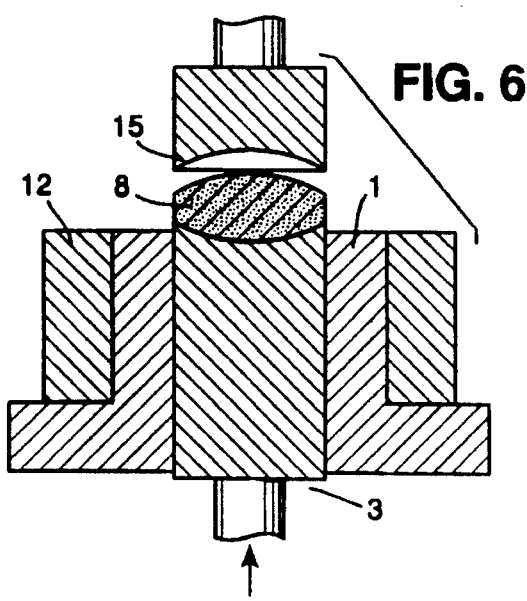
FIG. 6 is a schematic (in cross-section) illustrating the ejection of the shaped frozen formulation (predevice) from the die by the bottom punch.
Figure 7:
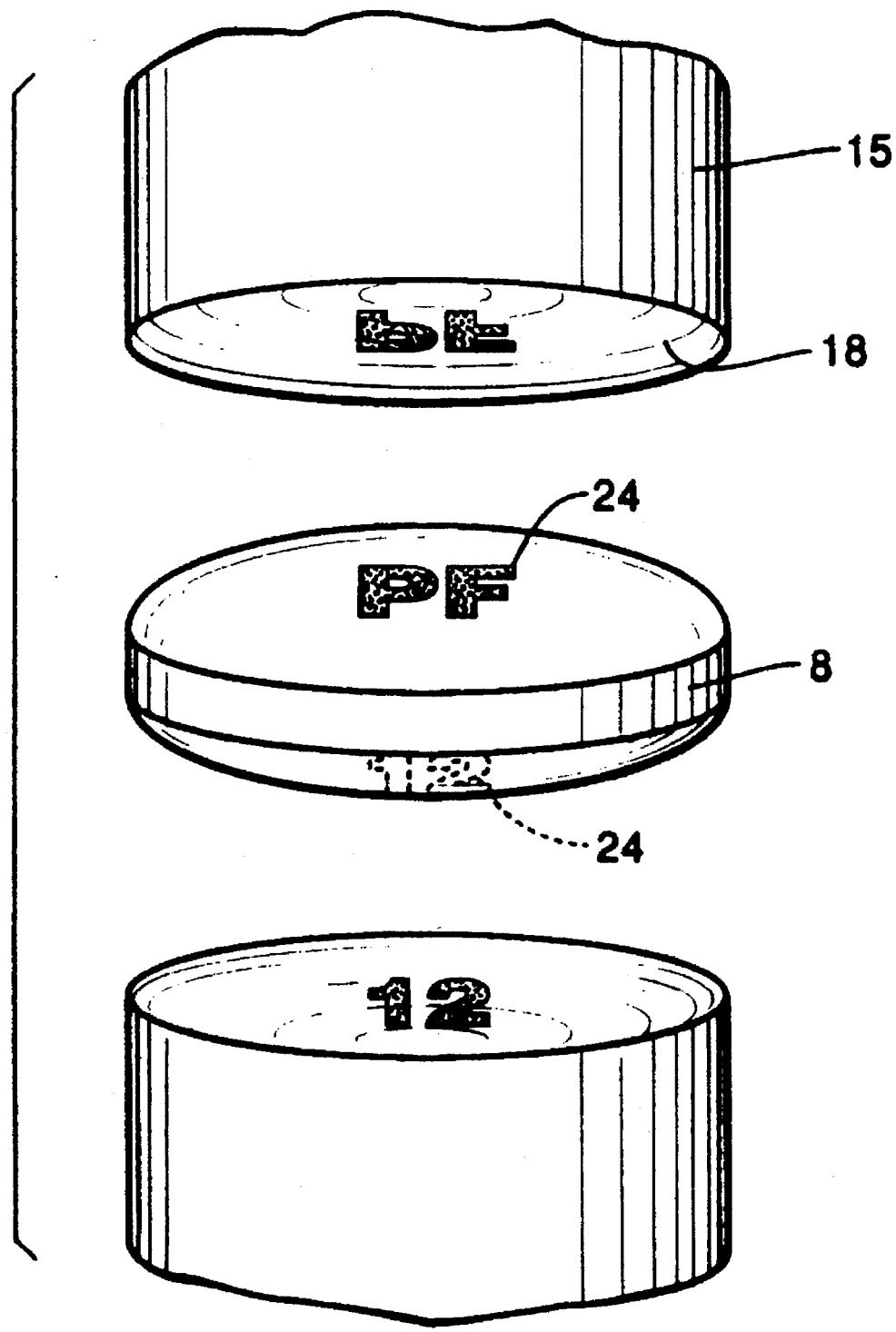
FIG. 7 is a schematic perspective view of the top punch, bottom punch and shaped predevice.

Referring to the drawings, there is illustrated in FIG. 1 a cylindrical die 1, through which a bottom punch 3 is mated by sliding. A filling apparatus 4 deposits the liquid formulation 6 in the cavity formed by the die 1 and punch 3. A refrigeration unit 12 is disposed in contact with the die 1. According to FIG. 2, the desired amount of liquid formulation 6 has been disposed in the cavity formed by the die 1 and punch 3, and is exposed to freezing temperatures by the refrigeration unit 12. According to FIG. 3, the frozen formulation 7 is disposed between the bottom punch 3, die 1 and top punch 15. According to FIG. 4, the shaped frozen formulation 8 has been compressed between the bottom punch 3, die 1 and top punch 15. According to FIG. 5, the top punch 15 is removed, and then the frozen shaped formulation (predevice) 8 is ejected from the die 1 by the action of the bottom punch 3, as depicted in FIG. 6. The shaped prodevice may then be conveniently lyophilized. FIG. 7 depicts the shaped imprints on the top 24 and bottom 27 of the frozen predevice 8 which were made by the corresponding molded shapes 18, 21 of the top punch 15 and bottom punch 3.

The freeze-dried devices are then available for use as desired. These devices may be used for the oral delivery of pharmaceutical agents to animals, including mammals, particularly man. These oral delivery devices can be administered as is or dissolved in water prior to administration. In addition, the devices may be utilized for alternative delivery as suppositories, ocular inserts, inplants, etc. Finally, these delivery devices may be used to deliver a variety of active ingredients to diverse environments. Exemplary ingredients include fertilizers for agricultural environments, food flavorings for cooking and baking, and sweeteners and cream for coffee and other drinks.

The devices and processes of this invention make a significant advance in the field of delivery devices. The devices are highly porous, which facilitates rapid dissolution or disintegration. The rapid dissolution or disintegration facilitates swallowing without water or mastication or both. The rapid dissolution rate facilitates the use of the device in those instances where such devices are desirable (e.g., veterinary delivery, pediatric patients, geriatric patients). The high strength maintains the device as an integral unit during conventional packaging, transporting and handling, thus assuring the physical integrity of the dosage form, and assuring that the patient receives the proper dosage. The molded shape aids in maintaining the device as an integral unit in comparison to compressionless tablets that can have weak, easily broken meniscuses. Finally, the molded shape also provides for identification on all surfaces with symbols, e.g., logos. In addition to the marketing advantages, this identification can also be used to aid in assuring a tablet's authenticity.

In the following Examples (below), the delivery devices strength and disintegration rates were determined by a friability test and a disintegration test.

Friability is a measure of tablet strength. The measurement is based on tablet weight loss, expressed as a percentage, after certain numbers of revolutions in the Vanderkamp Friabilator. A low friability value represents better tablet strength.

Disintegration time is measured by the Stoll-Gershberg method using the Erweka tester. The tablet is placed in a perforated basket which is immersed in a 37° C. water bath. During the test, the basket moves in an up-and-down motion. The time needed for complete disintegration of the tablet is recorded as the disintegration time.

The materials used in the following Examples are as follows:

| | |
|---|---|
| Water: | distilled |
| Gelatin: | 150 bloom; General Foods Corporation |
| Pectin: | low methoxyl pectin; Sunkist Growers |
| CARBOPOL 934P: | carbomer; The B. F. Goodrich Company |
| KLUCEL EF: | hydroxypropylcellulose; Aqualon Company |
| POVIDON C30: | poly(N-vinylpyrrolidone); GAF Corporation |
| Calcium chloride: | calcium chloride dihydrate; Fisher Scientific |
| Mannitol: | Ruger Chemical Company |
| Xylitol: | American Xyrofin Inc. |
| ASPARTAME: | Nutrasweet; Nutrasweet Company |
| Orange flavor: | natural and artificial orange flavor; Firmenich Inc. |
| Grape flavor: | spray dried natural and artificial grape flavor; Food Materials Corporation |
| FLUCONAZOLE: | anti-fungal agent; Pfizer Inc |
| MICROENCAPSULATED FLUCONAZOLE: | fluconazole coated with Surelease/Opadry.; 70% drug potency; Pfizer Inc |
| PIROXICAM: | anti-inflammatory agent; Pfizer Inc |
| PSEUDOEPHEDRINE HCl: | decongestant; Knoll Fine Chemical. |

EXAMPLE 1

Gelatin was dissolved in warm water (55° C.) followed by the addition of mannitol, aspartame, and the encapsulated orange flavor. Each 1,000 mg solution contained the following:

| Tablet A Ingredients | Mg/tablet |
|---|---|
| Water | (930) later removed |
| Gelatin | 25 |
| Mannitol | 35 |
| ASPARTAME | 5 |
| Orange flavor | 5 |
| TOTAL | (1000) 70 |

A die-and-punch assembly was lubricated with silicone grease and pre-cooled in a dry-ice container (−78° C.). The above solution was charged into the tableting die with the bottom punch in place. After the solution in the die was frozen and cooled to about 26° C., a pre-cooled top punch was placed into the die. Using a Carver press, a force of 5,000 pounds was applied to the punch to momentarily liquify the top surface of the frozen mass. After the pressure was released, the top punch was removed. The frozen, shaped tablet was then pushed out of the die. The water in the tablet was removed by lyophilization. The final tablet had the shape and the imprint in three dimensions from the tableting die and punches (0.375 inch by 0.875 inch oval, 0.250 inch thick). The porosity of the tablet was 93% based on the amount of water removed by lyophilization.

Friability after 100 revolutions: 0.0%.

Disintegration time: 4 seconds.

EXAMPLE 2

The same formulation as in Example 1 was charged into a pre-cooled die-and-punch assembly. The top punch was kept at 60° C. before being brought into contact with the frozen mass in the die. Using a Carver press, the punches were applied with a force of 1,000 pounds which was sufficient for the warm punch to momentarily liquify the surface of the frozen mass. The top punch was then removed and the tablet was pushed out of the die. The tablet was lyophilized as in Example 1 to yield a 93% porous tablet (Tablet B) which had the shape and the imprint in three dimensions from the tableting die and punches (0.375 inch by 0.875 inch oval, 0.250 inch thick).

Friability after 1000 revolutions: 0.0%.

Disintegration time: 4 seconds.

EXAMPLE 3

Solution A: Low-methoxyl pectin (5 g) was blended with warm water (150 g) in a blender for one minute and let stand for 5 minutes.

Solution B: Mannitol (25 g), calcium chloride dihydrate (0.25 g), and the encapsulated orange flavor (2 g) were added to water (275 g). The pH of this solution was adjusted to 3.2 with citric acid. The solution was heated to 80° C.

Solution A and solution B were mixed with stirring and allowed to cool. Following the procedure in Example 1, frozen tablets were made using the pre-cooled die and punches. Each 1,000 mg tablet contained the following:

| Tablet C Ingredients | Mg/tablet |
| --- | --- |
| Water | (929) later removed |
| Pectin | 11 |
| Mannitol | 55 |
| Calcium chloride | 0.6 |
| Orange flavor | 4.4 |
| TOTAL | (1000) 71 |

Using a Carver press, each tablet was three dimensionally molded and imprinted (0.375 inch by 0.875 inch oval, 0.250 inch thick) with a force of 5,000 pounds applied to the punches. The final, lyophilized tablet was 92.9% porous.

Friability after 100 revolutions: 0.0%.

Disintegration time: 22 seconds.

EXAMPLE 4

POVIDONE C30 was dissolved in water followed by the addition of mannitol, aspartame, and the encapsulated orange flavor. Each 1,000 mg solution contained the following:

| Tablet D Ingredients | Mg/tablet |
| --- | --- |
| Water | (930) later removed |
| POVIDON C30 | 25 |
| Mannitol | 35 |
| ASPARTAME | 5 |
| Orange flavor | 5 |
| TOTAL | (1000) 70 |

Three dimensionally molded and imprinted tablets (0.375 inch by 0.875 inch oval, 0.250 inch thick) of 93% porosity were made by following the procedure in Example 1.

Friability after 30 revolutions: 1.6%

Disintegration time: 2 seconds.

EXAMPLE 5

KLUCEL-EF (hydroxpropyt cellulose) was dissolved in water followed by the addition of mannitol, ASPARTAME, and the encapsulated orange flavor. Each 1,000 mg solution contained the following:

| Tablet E Ingredients | Mg/tablet |
| --- | --- |
| Water | (930) later removed |
| KLUCEL EF | 25 |
| Mannitol | 35 |
| ASPARTAME | 5 |
| Orange flavor | 5 |
| TOTAL | (1000) 70 |

Three dimensionally molded and imprinted tablets (0.375 inch by 0.875 inch oval, 0.250 inch thick) of 93% porosity were made by following the procedure in Example 1.

Friability after 30 revolutions: 1.4%.

Disintegration time: 12 seconds.

EXAMPLE 6

CARBOPOL-934P was dissolved in water followed by the addition of mannitel, aspartame, and the encapsulated orange flavor. Each 1,000 mg solution contained the following:

| Tablet E Ingredients | Mg/tablet |
| --- | --- |
| Water | (930) later removed |
| CARBOPOL 934P | 10 |
| Mannitol | 50 |
| ASPARTAME | 5 |
| Orange flavor | 5 |
| TOTAL | (1000) 70 |

Three dimensionally molded and imprinted tablets (0.375 inch by 0.875 inch oval, 0.250 inch thick) of 93% porosity were made by following the procedure in Example 1.

Friability after 30 revolutions: 5.6%.

Disintegration time: 4 seconds.

EXAMPLE 7

CARBOPOL 934P was dissolved in water followed by the addition of mannitol, ASPARTAME, the encapsulated orange flavor and FLUCONAZOLE. Each 1,052.5 mg solution contained the following:

| Tablet G Ingredients | Mg/tablet |
|---|---|
| Water | (930) later removed |
| Carbopol 934P | 10 |
| Mannitol | 50 |
| Aspartame | 7.5 |
| Fluconazole | 50 |
| Orange flavor | 5 |
| TOTAL | (1052.5) 122.5 |

EXAMPLE 8

Xylitol, mannitol, and the encapsulated orange flavor were dissolved in water. Each 1,000 mg solution contained the following:

| Tablet H Ingredients | Mg/tablet |
|---|---|
| Water | (650) later removed |
| Xylitol | 130 |
| Mannitol | 195 |
| Orange flavor | 25 |
| TOTAL | (1000) 350 |

Three dimensionally molded and imprinted tablets (0.95 cm by 2.22 cm oval, 0.64 cm thick) of 65% porosity were made by following the procedure in Example 1.

Friability after 30 revolutions: 3.3%.

Disintegration time: 2 seconds.

EXAMPLE 9

Gelatin was dissolved in warm water followed by the addition of mannitol, aspartame, microencapsulated fluconazole, xanthan gum and the encapsulated orange flavor. Each 1,521.6 mg solution contained the following:

| Tablet I Ingredients | Mg/tablet |
|---|---|
| Water | (1317) later removed |
| Gelatin | 40 |
| Mannitol | 10 |
| ASPARTAME | 5 |
| MICROENCAPSULATED FLUCONAZOLE | 143 |
| XANTHAN | 1.6 |
| Orange flavor | 5 |
| TOTAL | (1521.6) 204.6 |

Three dimensionally molded and imprinted tablets (0.375 inch by 0.875 inch oval, 0.350 inch thick) of 86.5% porosity were made by following the procedure in Example 1.

Friability after 100 revolutions: 0.0%.

Disintegration time: 14 seconds.

EXAMPLE 10

Gelatin was dissolved in warm water followed by the addition of mannitol, ASPARTAME, the encapsulated grape flavor, and pheudoephedrine hydrochloride. Each 1,000 mg solution contained the following:

| Tablet J Ingredients | Mg/tablet |
|---|---|
| Water | (900) later removed |
| Gelatin | 25 |
| Mannitol | 40 |
| ASPARTAME | 3 |
| PHEUDOEPHEDRINE HCl | 30 |
| Grape flavor | 2 |
| TOTAL | (1000) 100 |

Three dimensionally molded and imprinted tablets (0.375 inch by 0.875 inch oval, 0.225 inch thick) of 90% porosity were made by following the procedure in Example 1.

Friability after 100 revolutions: 0.0%.

Disintegration time: 1 second.

EXAMPLE 11

Gelatin was dissolved in warm water followed by the addition of mannitol, ASPARTAME, the encapsulated grape flavor, and PIROXICAM. Each 1,000 mg of PIROXICAM suspension contained the following:

| Tablet K Ingredients | Mg/tablet |
|---|---|
| Water | (900) later removed |
| Gelatin | 25 |
| Mannitol | 50 |
| ASPARTAME | 3 |
| PIROXICAM | 20 |
| Grape flavor | 2 |
| TOTAL | (1000) 100 |

Three dimensionally molded tablets (0.625 inch deep-round-concave, 0.175 inch thick) of 90% porosity were made by following the procedure in Example 1.

Friability after 100 revolutions: 0.0%.

Disintegration time: 1 second.

It should be understood that the invention is not limited to the particular embodiments described herein, but that various changes and modifications may be made without departing from the spirit and scope of this novel concept as defined by the following claims.

We claim:

1. A porous, compressed shaped delivery device comprising:

a) about 5% to about 95% water soluble polymer; and b) about 0.01 mg to about 1000 mg active agent; wherein said device has a porosity of at least about 85%, said porosity void of active agent and said device has a predetermined molded shape over the entire device surface.

2. The device as recited in claim 1 wherein said water soluble polymer is gelatin, pectin, hydroxypropyl cellulose, poly(N-vinylpyrrolidone) or carhomer.

3. The device as recited in claim 2 wherein said beneficial agent is a pharmaceutical agent.

4. The device as recited in claim 3 wherein said pharmaceutical agent is fluconazole, piroxicam or pheudoephedrine HCl, azithromycin, sertraline, or cetirizine.

5. The device as recited in claim 4 wherein said device comprises about 5% to about 30% water soluble polymer.

6. A method for making a porous shaped delivery device comprising:

a). disposing a formulation into a first die, said formulation comprising about 0.01 mg to about 1000 mg beneficial agent and about 1% to about 10% water soluble polymer;

b). freezing said formulation to form a frozen predevice;

c). contacting a second die with the exposed frozen predevice surface at a pressure, temperature and time sufficient to locally liquify, shape and refreeze said surface; and d). lyophilizing said frozen predevice to form said porous, shaped delivery device, said device having aporosity of about 85% to about 98%, said porosity void of active agent.

7. The method as recited in claim 6 wherein said formulation includes a water soluble polymer.

8. The method as recited in claim 7 wherein said formulation includes a pharmaceutical agent.

9. The method as recited in claim 8 wherein said formulation includes at least about 85% water.

10. The method as recited in claim 9 wherein said pressure and temperature ranges from 0.5 kg/cm$^2$ at 200° C. to 9,000 kg/cm$^2$ at −78° C. over a period of 1 second to 1 minute.

11. The method as recited in claim 9 wherein said water soluble polymer is gelatin, pectin, hydroxypropyl cellulose, poly(N-vinylpyrrolidone), or carbomer.

12. The method as recited in claim 11 wherein said pharmaceutical agent is fluconazole, piroxicam, pheudoephedrine HCl, azithromycin, sertraline, or cetirizine.

13. The method as recited in claim 12 wherein said pressure and temperature ranges from 2,500 kg/cm$^2$ at −30° C. to 450 kg/cm$^2$ at 60° C. over 1 second to 10 seconds.

14. The method as recited in claim 13 wherein said pharmaceutical agent is fluconazole and said water soluble polymers are gelatin and carhomer.

15. The method as recited in claim 14 wherein said device contacts a mold release material integral to or applied to said dies.

* * * * *